United States Patent [19]

Will

[11] 4,392,488
[45] Jul. 12, 1983

[54] JOINT SPLINT

[76] Inventor: Peter Will, Wiener Strasse 78, 6100 Darmstadt, Fed. Rep. of Germany

[21] Appl. No.: 267,388

[22] Filed: May 26, 1981

[30] Foreign Application Priority Data

May 27, 1980 [DE] Fed. Rep. of Germany ....... 3020083

[51] Int. Cl.³ .......................... A61F 3/00; A61F 5/00
[52] U.S. Cl. .................................. 128/80 R; 128/80 F
[58] Field of Search ................. 128/80 R, 80 C, 80 F; 3/22, 29

[56] References Cited

U.S. PATENT DOCUMENTS

| 2,208,275 | 7/1940 | McCann | 3/29 |
| 2,638,605 | 5/1953 | Johnson | 3/22 |
| 2,877,033 | 3/1959 | Koetke | 128/80 F |
| 3,785,372 | 1/1974 | Craig | 128/80 C |
| 3,902,482 | 9/1975 | Taylor | 128/80 F |
| 4,068,312 | 1/1978 | Ledesma | 128/80 C |
| 4,144,881 | 3/1979 | Chappell | 128/80 F |
| 4,215,442 | 8/1980 | Blatchford et al. | 3/22 |

Primary Examiner—Kyle L. Howell
Assistant Examiner—C. W. Shedd

[57] ABSTRACT

Device for the support of joints for orthopedic and surgical purposes, which permits use on the periphery or surface of the joint, in the principal plane of movement. The adaptation of the splint to, and its accompaniment of, the change in the configuration of the joint surface upon movements is assured by concatenation linkage of the joint splint, wherein the links, which are constructed as obtuse-angled bell cranks, are united to one another by articulations to form a chain such that, in the case of a radial movement of the splint links, they simultaneously produce a lengthening of the splint according to the principle of the Nuremberg scissors.

5 Claims, 7 Drawing Figures

JOINT SPLINT

BACKGROUND OF THE INVENTION

In the medical treatment of the joints of the body, measures are often necessary for the purpose of stabilizing the ligaments of the joints and supporting the joint moving organs. Circular elastic bandages enveloping the entire joint area, and corsets for the torso, or splint apparatus with built-in joints are used for this purpose. The manner in which the organic joints are constructed and surrounded by soft parts creates problems in treatment with mechanical joint stabilizing measures, and heretofore these problems have been solved but inadequately. In contrast to the stiff, flat-junction artificial joints of the art, body joints, on account of the irregular shape of the articulating joint surfaces, are characterized by an inconstant location of the joint axis. Monoaxial joints, such as are used in splint apparatus, are therefore impossible to center on body joints. Shear stresses in the apparatus during joint movements and shearing forces in the joint area are known, disadvantageous phenomena. Also the treatment of diseased joints with bandages and ortheses often entails difficulties, because considerable shifting occurs in the superficial, joint-enveloping soft parts in processes of movement. The elastic, stretchable materials used as bandages for the purpose are only to a limited extent adaptable to the constantly changing movements of the soft parts. The use of stronger, more rigid materials for the achievement of greater stability often involves compression and thrust by the therapeutic apparatus with resultant adverse effects on the soft parts and on the nerve and blood vessel pathways in the treated extremity.

SUMMARY OF THE INVENTION

The above-named disadvantages in the treatment of joint ailments are avoided by the splint design of the invention. In accordance with the invention, the splint is one for the supporting of joints for orthopedic or surgical purposes, characterized by the fact that it consists of a chain of obtuse-angled bell cranks, in which the preferably longer limb of each successive bell crank overlaps the one end of the corresponding limb of the preceding bell crank, and the fulcrum of each bell crank with the exception of the first is guided in a longitudinal slot at the end of the preferably longer limb of the preceding bell crank, and each fulcrum with the exception of the last is additionally connected by a crosslink to the end of the preferably shorter limb—the one not provided with the longitudinal slot—of the next succeeding bell crank such that, when the entire chain is flexed, the chain simultaneously lengthens according to the Nuremberg scissors principle.

In contrast to the joints commonly used in treatment splints, which have to be centered as much as possible on the axis of the body joints, the new splint is disposed in the chief plane of movement of the joint, on the periphery or surface of the joint, and it is fastened to the limbs or extremities of the joint. The manner in which the splint moves to accompany and adapt to the change in the form of the joint surface when movement occurs is determined by the concatenated character of the splint, which has articulations permitting the splint to vary its length in proportion to a radial movement of the individual links.

The dimensions of the individual links and the angle with which the splint links are made can be adapted to the special requirements. This applies, for example, to models for adults and children or to different stresses on the splint at the torso or adjacent the extremities, where for static reasons or reasons of circumference, the dimensions of the splint or of its individual links have to be adapted.

The slot-like aperture is likewise variable in accordance with the invention, because thereby the movement lengthwise of the splint can be predetermined in a particular direction, if necessary, by angling the slot.

The length of the splint can be determined by the number of assembled links. To obtain a broadening or strengthening in particular places or over the entire length of the splint, a plurality of parallel rows of links can be placed on correspondingly lengthened fulcrum shafts so as to form a plurality of parallel rows of chain links.

For the production of the joint splint it is preferable to use links premanufactured in series, which can be made, for example, of metals such as steel or aluminum, but also of plastics such as polyethylene, polypropylene, polyamide, polymethacrylate, polystyrene or reinforced, e.g., glass fiber-reinforced, products.

Advantageous is a combination of metal and plastic links so as to improve the mechanical load bearing capacity without substantially increasing the weight. For example, thin metal links of a thickness of 0.1 to, say, 5 mm, can be inserted between thicker plastic links (thickness 3–50 mm).

The lateral portions of the plastic links can be equipped with steel inserts, and hollow or skeletonized metal links can be used. Plastic spacers can be placed between metal links to increase the surface area of the splints in width. If soft materials such as rubber or soft PVC are used, the splint can be given elastic properties, and this can be limited by the use of appropriate individual links on certain areas.

A BRIEF DESCRIPTION OF THE DRAWINGS

The invention is illustrated by way of example in the accompanying drawings, in which.

DETAILED DESCRIPTION OF THE DRAWING

Figure 1:
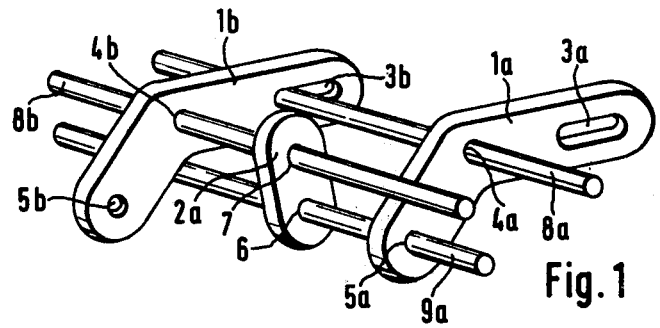
FIG. 1 is a perspective view of a joint splint according to the present invention.

In FIG. 1, two splint links 1a and 1b are represented, as well as a connecting link 2a. Each splint link 1a and 1b is of an angular configuration and provided with a guide slot 3a and 3b, and with two bores 4a and 4b as well as 5a and 5b. The bores 4a and 5a accommodate two rods as fulcrum shafts 8a and 9a. The splint link 1b is mounted at its guide slot 3b on the shaft 8a. The connecting link 2a, which is mounted at its bores 6 and 7 on the parallel shafts 8a and 9a produces a linkage between the splint links 1a and 1b.

Figure 2:
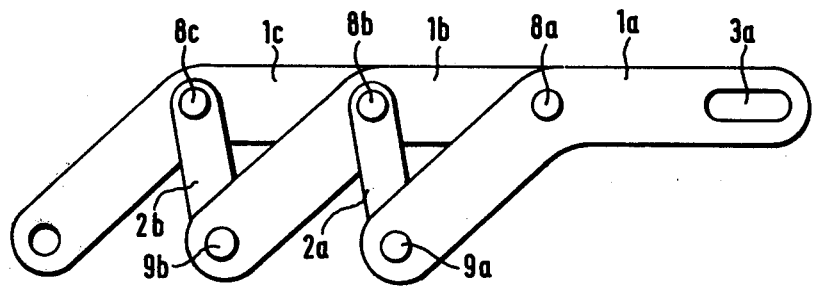
FIG. 2 is a side view of the joint splint of FIG. 1 in its starting position.

FIG. 2 shows the arrangement of three splint links 1a, 1b and 1c in a starting position.

Figure 3:
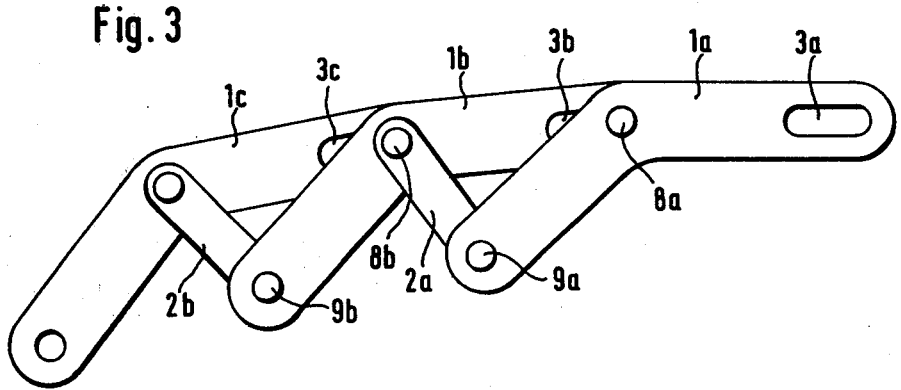
FIG. 3 is a side view showing the joint splint in downwardly bent position.

FIG. 3 demonstrates a possible movement of the subject of the invention, wherein it can be seen that the individual splint links 1a, 1b and 1c are now arranged in an arc with one another, and that the movement that has taken place is made up of two components. The splint links 1b and 1c have each advanced radially at an angle about the axis 9a and 9b, respectively, while the connecting links 2a and 2b serve for the deflection of the movement. It is furthermore seen that each splint link 1b and 1c is displaced from its starting position, lengthwise of the splint, as a second component of the movement, this movement being deflected by the guide slots 3b and 3c with the axes 8a and 8b.

Figure 4:
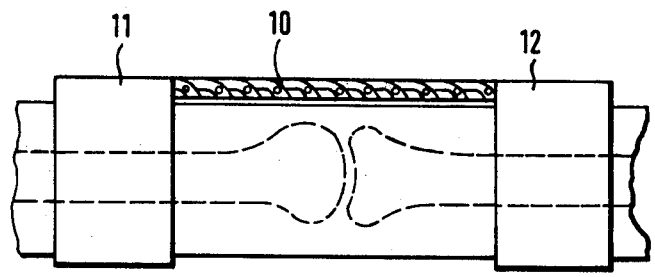
FIGS. 4 and 5 show the application of the joint splint to a limb.
Figure 5:
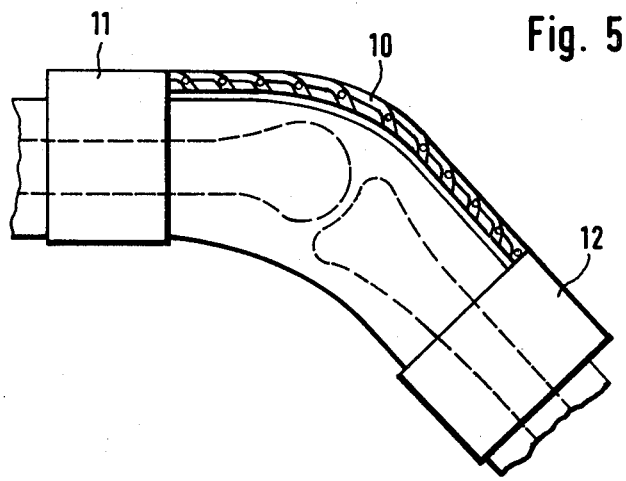

FIGS. 4 and 5 show an example of application. The concatenated splint 10 is fastened by cuffs 11 and 12 to the limbs or extremities on the proximal and distal sides of the joint, and placed over the stretching side of the joint. In the event of the flexion of the joint, the splint links are able to follow the joint surface and adapt to the resultant change of shape, due to the freedom of movement given them. Upon the extension of the joint, the splint links slide back together to their starting position.

Figure 6:
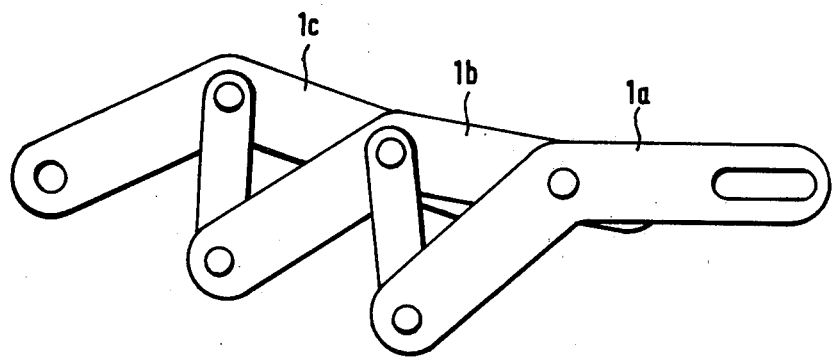
FIG. 6 is a side view of the joint splint of FIG. 1 bent upwardly.

FIG. 6 shows another possible movement in the splint. By an elongation of the guide slot, a movement of the splint links 1a, 1b and 1c opposite that of FIG. 3 can be made possible.

Figure 7:
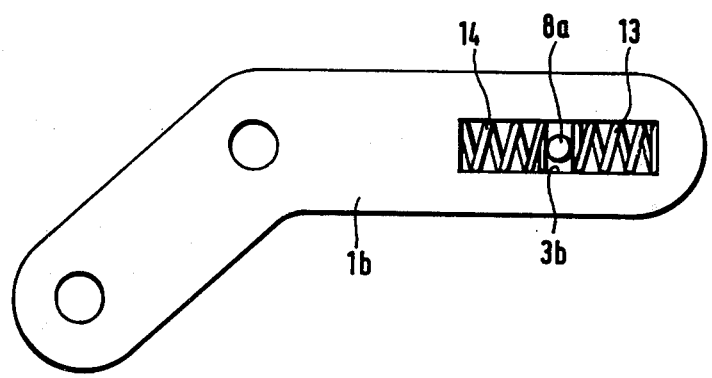
FIG. 7 is a side view of a modified splint link.

FIG. 7 shows an additional embodiment of the splint, in which two resilient elements 13 and 14 are inserted in a guide slot 3b of a link 1b, so that the movement of link 1b with respect to the axis 8a can be impeded or even facilitated, according to the requirements. The resilient elements can be used on only one side, if desired, in which case the movement of the splint is affected only in one desired direction.

The arrangement of the connecting links and splint links on parallel shafts permits only movements and changes in the shape of the splint in a plane parallel to their longitudinal axis. Kinking or acute-angle flexing along the length of the concatenated splint is excluded. The problem of joint guidance and stabilization of one functional direction is solved in an especially desirable manner by the peculiarities of the design of the concatenated splint. By covering the splint with resilient materials which adapt to the changing shape of the splint, mechanical irritation of the soft parts of the limb are largely prevented. The manner of the operation of the concatenated splint can be expanded and varied by modifications of design and mechanical additions as may appear expedient in the application. If not only guidance and stabilization of the joint are to be achieved, but also support of the joint moving organs, resilient elements can be inserted between the individual links of the splint, which either produce a return of the individual links to the neutral position or reinforce a movement in a given direction. Resilient elements or force storing means are suitable for this purpose which affect two links in each case (FIG. 7) or those which simultaneously span several links and are fastened, for example, to the ends of the splint.

If the movement of an ailing joint must be partially blocked, it is possible by blocking the individual splint links [to limit] the extent of the change of shape of the splint and thus to achieve a restriction by the splint of the operation of the joint, as for example by snapping a U-shaped clip in place or by turning threaded spindles so as to clamp up the radial movement or also the longitudinal movement of the splint links 1a or of the connecting links 2a.

Since the functioning of some organs of movement take place in different planes of movement, connecting elements can be installed between two or more splint links to permit an adaptation of the splint design to movements, either by articulations or by flexible connections. To assure a stable bearing of the splint structure on an organ of movement, a cuff or bandage circularly encompassing the organ of movement can be fastened to each of the splint links.

I claim:

1. A splint for the support of joints for orthopedic and surgical purposes, comprising: a chain of first, at least one intermediate, and last, obtusely angled bell cranks which are substantially identical replications, said bell cranks each having a fulcrum approximately at the intersection of first and second limbs, which limbs are oriented in like fashion along the length of said chain, with said first limbs of adjacent bell cranks overlapping and having, each separately, a slot therethrough adjacent the end distal from said fulcrum; each fulcrum, with the exception of that of said first bell crank, having an axle which is constrained to be guided within said slot of the overlapping adjacent first limb; each said second limb, excepting that of said first bell crank, having one end of a crosslink pivotally connected adjacent the end distal from said fulcrum; the other end of said crosslink being pivotally connected to said axle of the preceding adjacent bell crank in said chain, such that when said first limbs are aligned said chain has a first length and when said first limbs are misaligned by flexing said chain, said chain changes to a second length; and attachment means connected to said first and last bell cranks for securing said splint on both sides of a joint in an extremity of a patient.

2. A splint according to claim 1, wherein the limbs of the obtuse-angled bell crank have unequal length.

3. A splint according to claim 2, wherein said first limbs are longer than said second limbs.

4. A splint according to claim 2 or 3, wherein the crosslinks are articulated in each case to the shorter limb of the succeeding bell crank.

5. A splint according to claim 1, 2 or 3, wherein resilient elements are inserted into the longitudinal slots of the individual bell cranks, which elements act to bias the associated axle toward a middle portion of the associated slot.

* * * * *